(12) United States Patent
Dasgupta

(10) Patent No.: US 6,332,049 B1
(45) Date of Patent: Dec. 18, 2001

(54) LUMINESCENCE DETECTOR WITH LIQUID-CORE WAVEGUIDE

(75) Inventor: Purnendu K. Dasgupta, Lubbock, TX (US)

(73) Assignee: Global FIA, Inc., Gig Harbor, WA (US)

(*) Notice: Subject to any disclaimer, the term of this patent is extended or adjusted under 35 U.S.C. 154(b) by 0 days.

(21) Appl. No.: 09/490,186

(22) Filed: Jan. 22, 2000

(51) Int. Cl.$^7$ ...................................................... G02B 6/00
(52) U.S. Cl. ........................... 385/12; 385/125; 436/172
(58) Field of Search ............................ 436/172; 385/12, 385/125

(56) References Cited

U.S. PATENT DOCUMENTS

| | | | |
|---|---|---|---|
| 4,150,295 | 4/1979 | Wieder | 250/458 |
| 4,458,175 | 7/1984 | Weekley | 313/472 |
| 4,560,248 | 12/1985 | Cramp et al. | 350/96.34 |
| 4,772,453 | 9/1988 | Lisenbee | 422/52 |
| 4,786,478 | 11/1988 | Ahmed et al. | 422/186.03 |
| 5,004,913 | * 4/1991 | Kleinerman . | |
| 5,133,037 | 7/1992 | Yoon et al. | 385/132 |
| 5,165,773 | 11/1992 | Nath | 362/32 |
| 5,184,192 | 2/1993 | Gilby et al. | 356/246 |
| 5,343,550 | 8/1994 | Egalon et al. | 385/123 |
| 5,412,750 | 5/1995 | Nath | 385/125 |
| 5,416,879 | 5/1995 | Liu | 385/125 |
| 5,444,807 | 8/1995 | Liu | 385/125 |
| 5,477,357 | 12/1995 | Suzuki et al. | 359/67 |
| 5,570,447 | 10/1996 | Liu | 385/125 |
| 5,608,517 | 3/1997 | Munk | 356/246 |
| 5,793,789 | 8/1998 | Ben-Michael et al. | 372/50 |
| 5,881,185 | 3/1999 | Feth et al. | 385/11 |
| 6,011,882 | * 1/2000 | Dasgupta et al. . | |
| 6,016,372 | * 1/2000 | Fein et al. . | |

OTHER PUBLICATIONS

P. Lacki, A. Nowakowski, P. Dress, and H. Franke, "Liquid–Core Waveguide as a Fluorescence Sensor," Paper Presented at Eurosensors XII, Sep. 13–16, 1998, pp. 343–346.
Purnendu K., Dasgupta Et Al., "Luminescence Detection With a Liquid–Core Waveguide," Anal. Chem. 1999, 71, 1400–1407.
Jianzhong Li and Purnendu K., Dasgupta "Chemiluminescence Detection With a Liquid–Core Waveguide: Determination of Ammonium with Electrogenerated Hypochlorite Based on the Luminol–Hypochlorite Reaction," Analytica Chimica Acta 19882 (1999), 1–7.

* cited by examiner

Primary Examiner—Hung N. Ngo
(74) Attorney, Agent, or Firm—Reginald F. Roberts, Jr.

(57) ABSTRACT

A luminescence detector with a liquid-core waveguide. For detecting photoluminescence, the exciting radiation is provided transversely instead of axially, thus eliminating the need for monochromators and focusing optics. For detecting chemiluminescence, the chemiluminescent reagents are mixed in situ in the detector, thus eliminating time loss which results in loss of chemiluminescence. A further aspect of the invention is the electrogeneration of an unstable reagent for the production of chemiluminescence. The unstable reagent is generated in such a way that there is complete separation of anodic and cathodic products without the use of a physical barrier.

22 Claims, 3 Drawing Sheets

LUMINESCENCE DETECTOR WITH LIQUID-CORE WAVEGUIDE

BACKGROUND OF THE INVENTION

The present invention relates to the detection of luminescence. More particularly, the invention relates to novel apparati and methods for the detection of photoluminescence, and for the generation and detection of chemiluminescence, using a detector having a liquid-core waveguide (LCW).

In commercial, conventional, and state-of-the-art LCW photoluminescence detectors, the exciting illumination is provided axially with respect to the main axis of the detector tube. These prior-art luminescence detectors require monochromators and focusing optics. The present invention provides LCW luminescence detectors which can operate without monochromators or focusing optics, and provides a novel method for the generation of chemiluminescence.

SUMMARY OF THE INVENTION

The present invention in a first aspect provides a photoluminescence detector. The detector comprises (a) a liquid-core waveguide comprising a transparent tube having first and second ends, for containing a liquid which can emit photoluminescence; (b) a light source which can provide illumination suitable for exciting the liquid to emit photoluminescence, the radiation from the light source being provided transversely with respect to the liquid-core waveguide tube; and (c) a photodetector, for detecting photoluminescence emitted by the liquid in the liquid-core waveguide tube.

In a second aspect the invention provides a chemiluminescence detector. The detector comprises (a) a liquid-core waveguide comprising a tube having first and second ends, for containing a liquid which emits chemiluminescence; (b) a photodetector, for detecting chemiluminescence emitted by the liquid in the liquid-core waveguide tube; (c) a first passageway for introducing a first reagent into the first end of the liquid-core waveguide tube; (d) a second passageway for introducing a second reagent into the first end of the liquid-core waveguide tube, whereby the first and second reagents are mixed within the first end of the liquid-core waveguide tube to form the liquid emitting chemiluminescence; and (e) a third passageway for discharging the liquid emitting chemiluminescence from the second end of the liquid-core waveguide tube.

In a third aspect the invention provides an apparatus for electrogeneration, as an anodic or a cathodic product, of an unstable reagent for the production of chemiluminescence in a liquid-core waveguide chemiluminescence detector. The apparatus comprises (a) a cell having an anode and a cathode; (b) a source of current connected to the anode and to the cathode; (c) a first passageway for introducing into the cell at a point substantially midway between the anode and the cathode an electrolyte to be electrolyzed; (d) a second passageway for conveying an anodic product from the cell; (e) a third passageway for conveying a cathodic product from the cell; (f) a fourth passageway for introducing the anodic or the cathodic product into a liquid-core waveguide chemiluminescence detector having first and second ends; and (g) a fifth passageway for introducing into the liquid-core waveguide detector a second reagent which, when mixed with the unstable reagent comprising the anodic or the cathodic product, forms a liquid which emits chemiluminescence. The fourth and fifth passageways and the liquid-core waveguide detector are constructed and arranged so that the unstable reagent and the second reagent are mixed with one another as they enter the first end of the liquid-core waveguide detector, forming in situ in the liquid-core waveguide detector the chemiluminescent liquid, which flows through the liquid-core waveguide detector and is discharged from the second end of the liquid-core waveguide detector.

In a fourth aspect the present invention provides an electrochemical method of generating, as an anodic or a cathodic product, an unstable reagent for the production of chemiluminescence in a liquid-core waveguide chemiluminescence detector. The method comprises (a) providing a cell having an anode and a cathode; (b) providing electrical current to the anode and the cathode; (c) introducing into the cell through a first passageway at a point substantially midway between the anode and the cathode an electrolyte to be electrolyzed; (d) conveying an anodic product from the cell through a second passageway; (e) conveying a cathodic product from the cell through a third passageway; (f) introducing the unstable reagent comprising the anodic or the cathodic product into a liquid-core waveguide chemiluminescence detector having first and second ends; and (g) introducing into the liquid-core waveguide detector through a fifth passageway a second reagent which, when mixed with the unstable reagent, forms a liquid which emits chemiluminescence. The fourth and fifth passageway and the liquid-core waveguide detector are constructed and arranged so that the unstable reagent and the second reagent are mixed with one another as they enter the first end of the liquid-core waveguide detector, thereby forming in situ in the liquid-core waveguide detector the chemiluminescent liquid, which flows through the liquid-core waveguide detector and is discharged from the second end of the liquid-core waveguide detector.

In a fifth aspect the invention provides an apparatus for the electrogeneration and separation of anodic and cathodic products. The apparatus comprises (a) a cell having an anode and a cathode; (b) a source of current connected to the anode and to the cathode; (c) a first passageway for conveying to the cell at a point substantially midway between the anode and the cathode an electrolyte to be electrolyzed; (d) a second passageway for conveying an anodic product from the cell; (e) a third passageway for conveying a cathodic product from the cell; and (f) means for simultaneously and continuously passing the electrolyte through the cell, the anodic product through the second passageway, and the cathodic product through the third passageway, thereby providing a flow-through system for the electrolysis of the electyrolyte, and for the separate recovery of the anodic and cathodic products.

In a sixth aspect the present invention provides a method for the electrogeneration and separation of anodic and cathodic products. The method comprises (a) providing a cell having an anode and a cathode; (b) connecting a source of current to the anode and to the cathode; (c) conveying to the cell through a first passageway disposed substantially midway between the anode and the cathode an electrolyte to be electrolyzed while (d) conveying an anodic product from the cell through a second passageway and a cathodic product from the cell through a third passageway, thereby providing continuous flow through the cell and the first, second, and third passageways, and separation of the anodic and cathodic products.

In a seventh aspect, the invention provides a liquid-core waveguide chemiluminescence detector. The detector comprises (a) a tubular member made of a material having a refractive index less than that of water; (b) a chemiluminescent solution disposed within and contained by the tubular member; and (c) a photodetector, for detecting the chemiluminescence emitted by the solution.

In an eighth aspect, the present invention provides a method for detecting chemiluminescence using a liquid-core waveguide. The method comprises (a) providing a liquid-core waveguide tube having a refractive index less than that of water; (b) disposing in the tube a water solution of a material which emits chemiluminescence; and (c) detecting the chemiluminescence which is emitted by the solution.

DETAILED DESCRIPTION OF THE INVENTION

Figure 1:
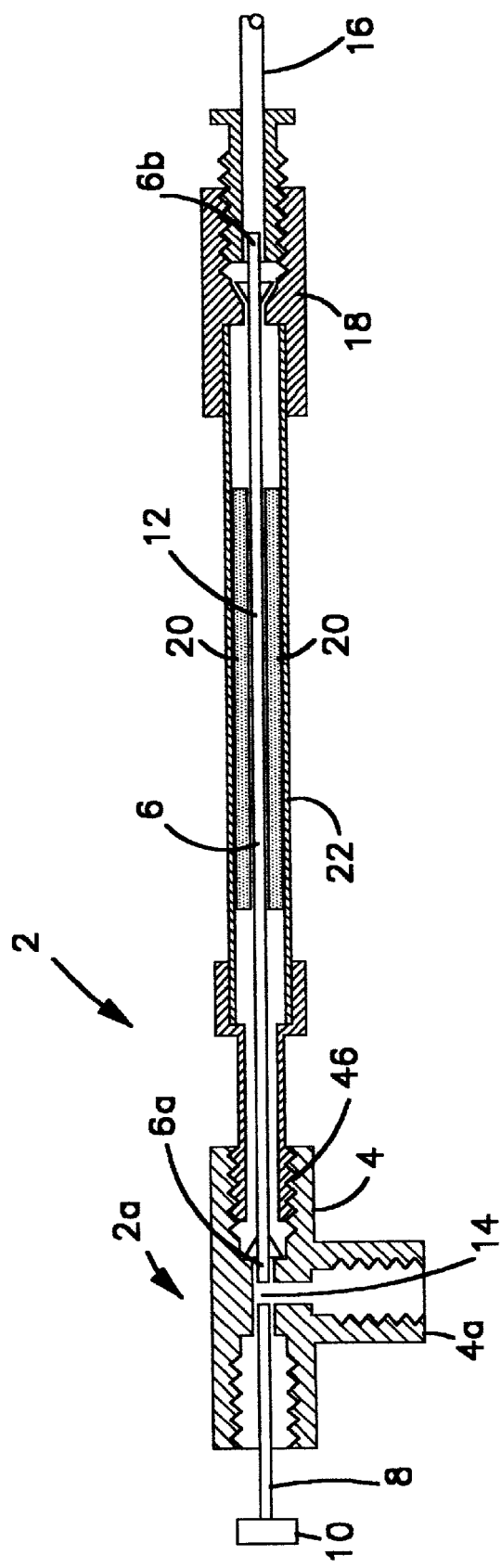
FIG. 1 is a schematic representation of a photoluminescence detector, made in accordance with the principles of the present invention.

More specifically, reference is made to FIG. 1, in which is shown a photoluminescence detector, made in accordance with the principles of the present invention, and generally designated by the numeral 2. The photoluminescence detector 2 comprises an opaque T-shaped member 4 which constitutes a first end 2a of the detector 2, and which comprises first and second arms 4a and 4b. In the center of the T-shaped member 4, a liquid-core waveguide (LCW) tube 6 abuts against an acrylic or silica optical fiber 8 that is coupled to a photodetector 10. The LCW tube 6 is made of or coated with an amorphouse fluoropolymer which is a copolymer of tetrafluoroethylene and perfluoro-2,2-dimethyl-1,3-dioxole, marketed under the registered trademark TEFLON AF® by E. I. Dupont de Nemours, a corporation of Wilmigton, Del. The tube 6 has a refractive index less than that of water.

A solution 12 in water of a substance capable of emitting photoluminescence enters the first end 2a of the photoluminescence detector 2 through the perpendicular first arm 4a of the T-shaped member 4, enters a first end 6a of the LCW tube 6 through the gap 14 between the tube 6 and the optical fiber 8, and flows through the tube 6 to its second end 6b, where a connecting tubing 16 is disposed in a chromotagraphic male-male union 18. The second end 6b of the LCW tube 6 is connected to the waste tubing 16 by compression-fitting the union 18.

A light source 20 illuminates the LCW tube 6. The light source 20 has a transverse orientation with respect to the LCW tube 6. Preferably, the light source 20 is substantially perpendicular to the LCW tube 6. More preferably, a plurality of lamps circumscribe the LCW tube 6. Most preferably, the lamps are disposed coaxially around the LCW tube 6. For a subminiature fluorescent lamp or light-emitting diode (LED) excitation source, the LED's being in single or arrayed configuration, an opaque tubular shell 22, which fits within the hub of a nut (not shown) in the T-shaped member 4 and within the inner portion of the union 18, which is drilled out to accommodate the tubular shell 22, shields the LCW tube 6 from external illumination. Electrical leads (not shown) to the light source 20 are brought through the walls of the tubular shell 22. The inside surface of the shell 22 is beneficially polished to improve excitation-light throughput.

The construction and geometrical arrangement of the photoluminescence detector 2 makes it possible to operate the detector 2 without monochromators, although limits of detection (LOD) are improved by the inclusion of monochromators. The construction and geometric arrangement of the detector 2 are such that it is particularly simple to fabricate the detector 2 in a flow-through configuration and have the photoluminescent radiation coupled to the photodetector 10 by the optical fiber 8. No focussing optics are necessary.

Figure 2:
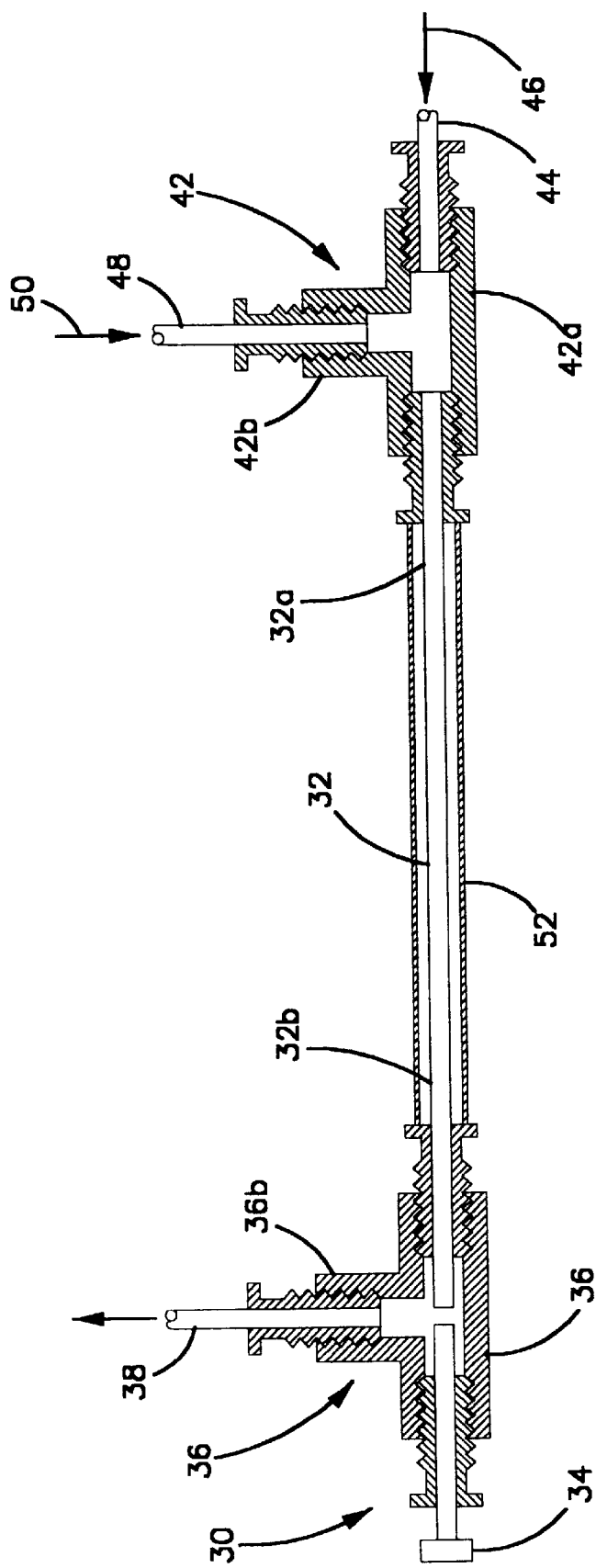
FIG. 2 is a schematic representation of a chemiluminescence detector, made in accordance with the principles of the present invention.

Reference is now made to FIG. 2, in which is shown a chemiluminescence detector, made in accordance with the principles of the present invention, and generally designated by the numeral 30. The chemiluminescence detector 30 includes a LCW tube 32 having first and second ends 32a and 32b, respectively. The LCW tube 32 is made of or coated with the same amorphous fluoropolymer, TEFLON AF®, as the LCW tube 6 shown in FIG. 1 as a component of the photoluminescence detector 2.

The second end 32b of the LCW tube 32 is butt-joined to a black-jacketed fused silica optical fiber 34 through a first arm 36a of a first opaque T-shaped member 36. The second arm 36b of the first T-shaped member 36 is utilized as a fluid outlet comprising a waste tube 38. The optical fiber 34 is connected to a miniature photomultiplier tube 40 containing its own power supply.

At the first end 32a of the LCW tube 32 is disposed a second opaque T-shaped member 42 having first and second arms 41a and 42b, respectively. A first opaque polymeric tube 44 brings in a stream of a first liquid 46 through the first arm 42a of the second T-shaped member 42, while a second opaque polymeric tube 48 is used to introduce a stream of a second liquid 50 through the second arm 42b of the second T-shaped member 42.

The entire length of the LCW tube 32 is jacketed with an exterior stainless-steel tube 52 to protect the LCW tube 32 from ambient light.

The spatial and geometrical arrangement of the chemiluminescence detector 30 ensures that the mixing of the first and second liquids 46 and 50, which produces the chemiluminescence, occurs within the detector 30. This internal in situ mixing ensures that the delay between the reaction which produces the chemiluminescence and the reception by the photomultiplier tube 40 of the light emitted by the chemiluminescence is controlled and determined only by the speed of light; hence, from an empirical, operational, and practical point of view, there is no delay whatsoever. The detector 30 is suitable for detecting chemiluminescence emitted by even diffusion-limited reactions, without special cell designs or large-area photomultiplier tubes.

Figure 3:
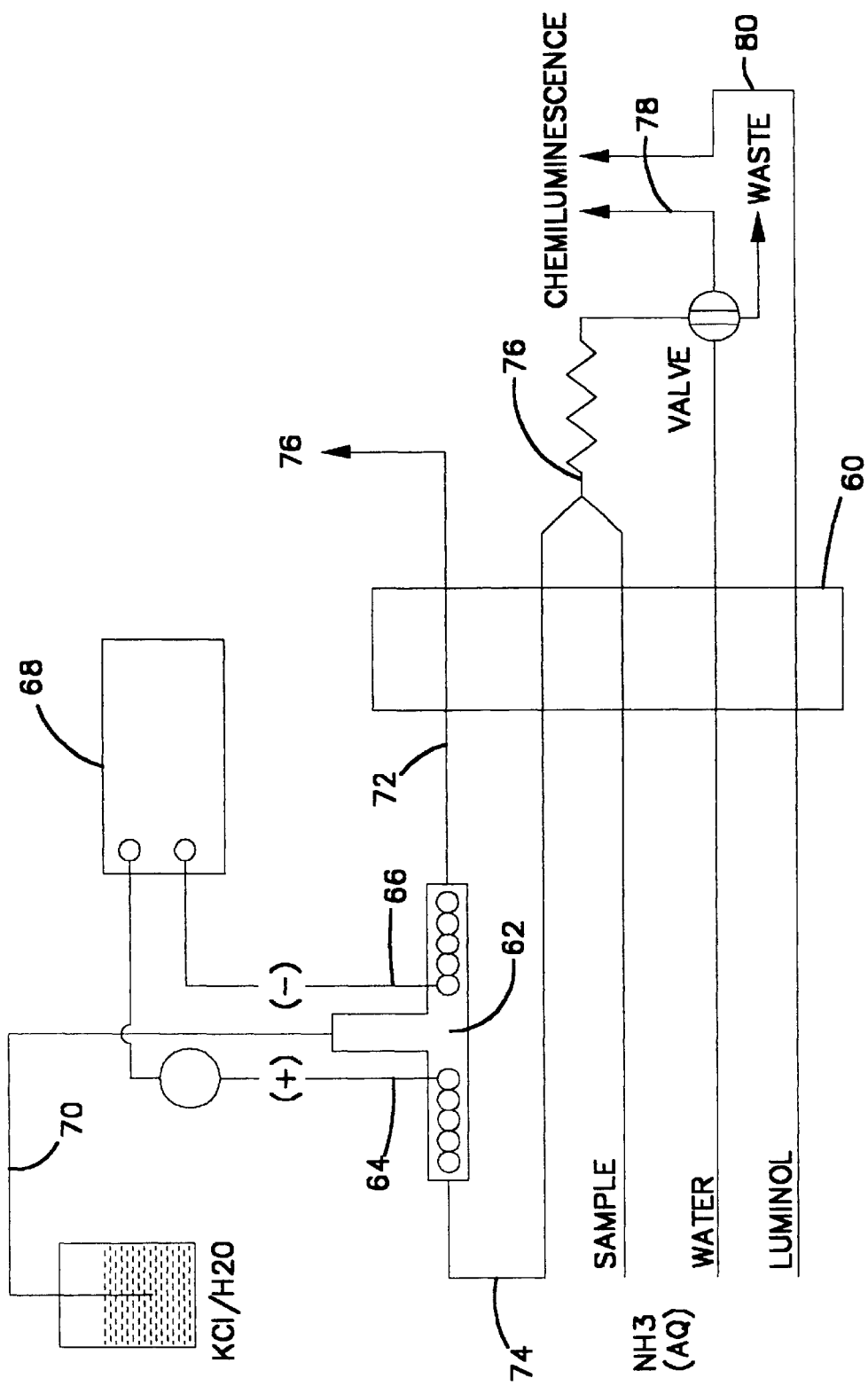
FIG. 3 is a flow diagram of an analysis system for the determination of chemiluminescence using an unstable reagent generated by electrolysis.

Reference is now made to FIG. 3, which is a flow diagram for the efficient and stable electrogeneration of an unstable reagent by a method which results in the complete separation of anodic and cathodic products. Separation of the electrolytic products is effected by flow hydrodynamics rather than by the use of membrane or frit-based barriers which generally increase the voltage drop and typically require the use of a potentiostatted system.

A peristaltic pump 60 passes a solution of an alkali-metal chloride in water through an electrolytic cell in which are disposed an anode 64 and a cathode 66 energized by a constant-current power supply 68. The alkali-metal chloride solution is conveyed to the cell 62 through a first passageway 70 which is disposed substantially midway between the anode 64 and the cathode 66. The cathodic product, a solution in water of an alkali-metal hydroxide, is pumped to waste through a second passageway 72. The anodic product, a solution in water of an alkali-metal salt of hypochlorous acid, is sent through a third passageway 74 concurrently with a stream of water and a solution of ammonia in water through a mixing coil 76. The diluted solution of the alkali-metal hypochlorite and ammonia is conveyed to the chemiluminescence detector 30 (FIG. 2) through a fourth passageway 78 and tube 44. At the same time a solution of luminol in water is introduced into the chemiluminescence detector 30 through through a fifth passageway 80 and tube 48. Mixing of the two streams is instantaneous, and the chemiluminescence thereby generated is detected by photomultiplier tube 40.

Various aspects of the invention will now be illustrated by the following examples of its use.

EXAMPLE I

Using the photoluminescence detector 2 shown in FIG. 1, a solution of formaldehyde in water was reacted with cyclohexanedione and ammonium acetate to form a product which was photoexcited to fluorescence. The concentration of formaldehyde was one-hundred nanomolar (100 nM). An ultraviolet light-emitting diode emitting approximately one milliwatt optical power at 370 nm was the excitation source. The photodetector 10 was a Hamamatsu H 5874 photomultipler tube (PMT) detector provided with a No. 856 (blue) plastic filter. With the photmultiplier gain set at fifty-five percent of maximum, the intensity of fluorescence was from about fifteen millivolts (15 mV) to about twenty millivolts (20 mV).

EXAMPLE II

Ammonia was pretreated with sodium sulfite and o-phthaldehyde to form 1-sulfonatosoindole, a fluorogenic derivative. This derivative was then photoexcited and the resultant fluorescence measured at 425 nm using the photoluminescence detector 2 shown in FIG. 1. The detection limit was 35 nM, using a blue/ultraviolet-sensitized photoiodide as the photodetector 10 with integral amplifier (Burr-Brown OPT 301) and a blue (No. 856) plastic filter.

EXAMPLE III

A 29-mm long array consisting of fourteen LED's connected in parallel, each LED having its own current-limiting resistor, was constructed by removing much of the epoxy molding from each LED (from both the top and the sides), cementing the LED's together with epoxy adhesive, and polishing the top of the array to create a flat surface. Using the photoluminescence detector 2 shown in FIG. 1, the LED array was placed in close lateral proximity to the LCW tube 6. A Hamamatsu avalanche photoiodide detector (APD) served as the photodetector 10. Fifteen microliters of a 670 nM solution of methylene blue in water with a five millimolar (5 mM) solution of hydrochloric acid in water as carrier was illuminated by a 660 nm red LED array (as described above). The apparatus was provided with a No. 35136 plastic filter. The intensity of fluorescence detected by the APD was from about 150 mV to about 170 mV, and the LOD was 50 nM at a signal/noise (S/N) ratio of three.

EXAMPLE IV

Two arrays of six ultrabright gallium nitride (GaN) green LED's each were deployed on opposite sides of the LCW tube 6 in the photoluminescence detector 2 shown in FIG. 1. A Hamamatsu H 5874 photomultiplier tube (PMT) with a No. 806 plastic filter was used as the photodetector 10. Twelve microliters of a 3 nM solution of Rhodamine 560 in water were illuminated with the LED arrays, and a fluorescent intensity of from about 230 mV to about 245 mV was registered by the PMT serving as the photodetector 10. The LOD at a S/N ratio of three was estimated to be less than or equal to one nanomolar.

EXAMPLE V

Luminol stock solution (50 nM) was prepared from 3-aminophalhydrazide in 0.01 M aqueous sodium-hydroxide solution. Sodium hypochlorite stock solution was a five percent by weight (5% w/w) solution in water of sodium hypochlorite (Baker Analyzed), standardized iodometrically. The stock solutions were, just prior to use, diluted successively with distilled deionized water. Ammonium stock solution (0.1 M) was prepared weekly from reagent-grade ammonium chloride and distilled, deionized water. Carbonate buffer solution was prepared from sodium carbonate and distilled deionized water, and adjusted to the desired pH with 2 M hydrochloric acid or sodium hydroxide in water. A glass electrode was used to measure pH.

Using the chemiluminescence detector 30 shown in FIG. 2 and a seventy-percent gain setting on the PMT 40, a 40 micromolar solution of sodium hypochlorite in water was introduced through tube 46 into the first end 32a of the LCW tube 32, while a one millimolar solution of luminol in water was simultaneously introduced through tube 48 into the first end 32a of the tube 32. Chemiluminescence registered by the PMT 40 was from about 2.72 to about 2.78 volts.

EXAMPLE VI

Using the same reagents as in Example V, the solutions of sodium hypochlorite and luminol were mixed "head-to-head" through the first arm 42a of the second T-shaped member 42, by inserting the first end 32a of the LCW tube 32 through the first arm 41a of the second T-shaped member as far into the cavity of the T-shaped member 42 as possible. Under these conditions the chemiluminescence measured by the PMT 40 was from about 1.37 to about 1.40 volts.

EXAMPLE VII

Normally, in the electrogeneration of reagents, it is critical to avoid mixing the anodic and cathodic products. In the prior art this is generally accomplished with mass-transfer barriers such as ion-selective membranes or fine-porosity frits between the electrodes. This example illustrates a simple arrangement which results in complete separation of the two electrode products, by means of a simple, low-dispersion, flow-through design. The basic concept is that the reagent-generation electrolyte enters a point between the electrodes and flows in opposite directions, sweeping past the electrodes.

As illustrated in FIG. 3, a water solution of potassium chloride was electrolyzed to produce a solution of potassium hydroxide, which was discharged to waste, and a solution of potassium hypochlorite, which was mixed with a water solution of ammonia. The mixture of potassium hypochlorite and ammonia solutions, along with dilution water, was routed through the tube 46 to the LCW tube 32 of the chemiluminescence detector 30 shown in FIG. 2, with the PMT 40 gain set at eighty percent. At the same time, a water solution of luminol was introduced through the tube 48 into the LCW tube 32 of the detector 30. Mixing of the two streams was instantaneous. The intensity of chemiluminescence generated by reaction between the reagents in the two streams is shown in Table I for hypochlorite generated by a ten-microampere current.

TABLE I

| Ammonia Concentration (micromoles per liter) | Intensity (volts) |
| --- | --- |
| 0 | 3.59 |
| 2 | 3.25 |
| 4 | 2.76 |
| 6 | 2.31 |
| 8 | 1.86 |
| 10 | 1.40 |
| 12 | 1.00 |
| 14 | 0.85 |

While certain embodiments and details have been used to illustrate the present invention, it will be apparent to those skilled in the art that many modifications are possible without departing from the basic concept of the invention.

Further details of the present invention are provided by the following scientific papers, which are hereby incorporated by reference:

(a) Purnendu K. Dasgupta et al., "Luminescence Detection with a Liquid Core Waveguide," *Anal. Chem.* 1999, 71, 1409–1407.

(b) Jianzhong Li and Purnendu K. Dasgupta, "Chemiluminescence Detection with a Liquid Core Waveguide: Determination of Ammonium with Electrogenerated Hypochlorite Based on the Luminol-Hypochlorite Reaction," *Analytica Chimica Acta* 19882 (1999), 1–7.

I claim:

1. A photoluminescence detector, comprising:
   (a) a liquid-core waveguide comprising a transparent tube having first and second ends, for containing a liquid which can emit photoluminescence;
   (b) a light source which can provide radiation suitable for exciting the liquid to emit photoluminescence, the radiation from the light source being provided transversely with respect to the liquid-core waveguide tube; and
   (c) a photodetector, for detecting photoluminescence emitted by the liquid in the liquid-core waveguide tube;
the liquid-core waveguide tube being made of or coated with an amorphous fluoropolymer which is a copolymer of tetrafluoroethylene and perflluoro-2,2-dimethyl-1,3-dioxole.

2. A photoluminescence detector, comprising:
   (a) a liquid-core waveguide comprising a transparent tube having first and second ends, for containing a liquid which can emit photoluminescence;
   (b) a light source which can provide radiation suitable for exciting the liquid to emit photoluminescence, the radiation from the light source being provided transversely with respect to the liquid-core waveguide tube;
   (c) a photodetector, for detecting photoluminescence emitted by the liquid in the liquid-core waveguide tube;
   (d) an optical fiber optically connecting the photodetector to the first end of the liquid-core waveguide tube; and
   (e) a hollow T-shaped opaque member, for holding the optical fiber and the first end of the liquid-core waveguide tube in alignment with one another, and for providing an inlet for the liquid to be contained by the liquid-core waveguide tube.

3. A photoluminescence detector, comprising:
   (a) a liquid-core waveguide comprising a transparent tube having first and second ends, for containing a liquid which can emit photoluminescence;
   (b) a light source which can provide radiation suitable for exciting the liquid to emit photoluminescence, the radiation being provided transversely with respect to the liquid-core waveguide tube;
   (c) a photodetector, for detecting photoluminescence emitted by the liquid in the liquid-core waveguide tube;
   (d) a first passageway for admitting the liquid to the first end of the liquid-core waveguide tube; and
   (e) a second passageway for discharging the liquid from the second end of the liquid-core waveguide tube;
the first and second passageways and the liquid-core waveguide tube being constructed and arranged so that the liquid enters the first passageway flows through the first passageway into the first end of the liquid-core waveguide tube, flows through the liquid-core waveguide tube, and is discharged from the second end of the liquid-core waveguide tube through the second passageway; the first passageway comprising a first arm of a hollow T-shaped member having first and second arms perpendicular to one another.

4. A photoluminescence detector, comprising:
   (a) a liquid-core waveguide comprising a transparent tube having first and second ends, for containing a liquid which can emit photoluminescence;
   (b) a light source which can provide radiation suitable for exciting the liquid to emit photoluminescence, the radiation from the light source being provided transversely with respect to the liquid-core waveguide tube;
   (c) a photodetector, for detecting photoluminescence emitted by the liquid in the liquid-core waveguide tube; and
   (d) an opaque tubular shell enclosing the waveguide and the light source, to provide isolation from external illumination when the light source is a fluorescent lamp or a light-emitting diode.

5. A photoluminescence detector, comprising:
   (a) a liquid-core waveguide comprising a transparent tube having first and second ends, for containing a liquid which can emit photoluminescence;
   (b) a light source which can provide radiation suitable for exciting the liquid to emit photoluminescence, the radiation from the light source being provided transversely with respect to the liquid-core waveguide tube; and
   (c) a photodetector, for detecting photoluminescence emitted by the liquid in the liquid-core waveguide tube;
wherein the radiation from the light source is perpendicular to the liquid-core waveguide tube.

6. A chemiluminescence detector, comprising:
   (a) a liquid-core waveguide comprising a tube having first and second ends, for containing a liquid which emits chemiluminescence;
   (b) a photodetector, for detecting chemiluminescence emitted by the liquid in the liquid-core waveguide tube;
   (c) a first passageway for introducing a first reagent into the first end of the liquid-core waveguide tube;
   (d) a second passageway for introducing a second reagent into the first end of the liquid-core waveguide tube, whereby the first and second reagents are mixed within the first end of the liquid-core waveguide tube to form the liquid emitting chemiluminescence; and (e) a third passageway for discharging the liquid emitting chemiluminescence from the second end of the liquid-core waveguide tube.

7. The chemiluminescence detector of claim 6, further comprising:

(f) an optical fiber optically connecting the photodetector to the second end of the liquid-core waveguide tube.

8. An apparatus for electrogeneration, as an anodic or a cathodic product, of an unstable reagent for the production of chemiluminescence in a liquid-core waveguide chemiluminescence detector, the apparatus comprising:

(a) a cell having an anode and a cathode;

(b) a source of current connected to the anode and to the cathode;

(c) a first passageway for introducing into the cell at a point substantially midway between the anode and the cathode an electrolyte to be electrolyzed;

(d) a second passageway for conveying an anodic product from the cell;

(e) a third passageway for conveying a cathodic product from the cell;

(f) a fourth passageway for introducing the anodic or the cathodic product into a liquid-core waveguide chemiluminescence detector having first and second ends; and (g) a fifth passageway for introducing into the liquid-core waveguide detector a second reagent which, when mixed with the unstable reagent comprising the anodic or the cathodic product, forms a liquid which emits chemiluminescence;

the fourth and fifth passageways and the liquid-core waveguide detector being constructed and arranged so that the unstable reagent and the second reagent are mixed with one another as they enter the first end of the liquid-core waveguide detector, forming in situ in the liquid-core waveguide detector the chemiluminescent liquid, which flows through the liquid-core waveguide detector and is discharged from the second end of the liquid-core waveguide detector.

9. An electrochemical method of generating, as an anodic or a cathodic product, an unstable reagent for the production of chemiluminescence in a liquid-core waveguide chemiluminescence detector, the method comprising the steps of:

(a) providing a cell having an anode and a cathode;

(b) providing electrical current to the anode and to the cathode;

(c) introducing into the cell through a first passageway at a point substantially midway between the anode and the cathode an electrolyte to be electrolyzed;

(d) conveying an anodic product from the cell through a second passageway;

(e) conveying a cathodic product from the cell through a third passageway;

(f) introducing the unstable reagent comprising the anodic or the cathodic product into a liquid-core waveguide chemiluminescence detector through a fourth passageway, the liquid-core waveguide chemiluminescence detector having first and second ends; and (g) introducing into the liquid-core waveguide detector through a fifth passageway a second reagent which, when mixed with the unstable reagent, forms a liquid which emits chemiluminescence;

the fourth and fifth passageways and the liquid-core waveguide detector being constructed and arranged so that the unstable reagent and the second reagent are mixed with one another as they enter the first end of the liquid-core waveguide detector, thereby forming in situ in the liquid-core waveguide detector the chemiluminescent liquid, which flows through the liquid-core waveguide detector and is discharged from the second end of the liquid-core waveguide detector.

10. The method of claim 9, wherein the electrolyte is a solution of an alkali-metal chloride in water.

11. The method of claim 9, wherein the unstable reagent is the anodic product.

12. The method of claim 11, wherein the anodic product is an alkali-metal salt of hypochlorous acid.

13. The method of claim 12, wherein the second reagent is a solution of luminol in water.

14. An apparatus for the electrogeneration and separation of anodic and cathodic products, the apparatus comprising:

(a) a cell having an anode and a cathode;

(b) a source of current connected to the anode and to the cathode;

(c) a first passageway for conveying to the cell at a point substantially midway between the anode and the cathode an electrolyte to be electrolyzed;

(d) a second passageway for conveying an anodic product from the cell;

(e) a third passageway for conveying a cathodic product from the cell; and (f) means for simultaneously and continuously passing the electrolyte through the cell, the anodic product through the second passageway, and the cathodic product through the third passageway, thereby providing a flow-through system for the electrolysis of the electrolyte, and for the separate recovery of the anodic and cathodic products.

15. A method for the electrogeneration and separation of anodic and cathodic products, the method comprising the steps of:

(a) providing a cell having an anode and a cathode;

(b) connecting a source of current to the anode and to the cathode; and (c) conveying to the cell through a first passageway disposed substantially midway between the anode and the cathode an electrolyte to be electrolyzed while (d) conveying an anodic product from the cell through a second passageway and a cathodic product from the cell through a third passageway, thereby providing continous flow through the cell and the first, second, and third passageways, and separation of the anodic and cathodic products.

16. A liquid-core waveguide chemiluminescence detector, comprising:

(a) a tubular member made of a material having a refractive index less than that of water;

(b) a chemiluminescent solution in water, disposed within and contained by the tubular member; and (c) a photodetector, for detecting the chemiluminescence emitted by the solution;

wherein the tubular member is made of or coated with an amorphous fluoropolymer which is a copolymer of tetetrafluoroethylene and perfluoro-2,2-dimethyl-1,3-dioxole.

17. A method for detecting chemiluminescence using a liquid-core waveguide, the method comprising the steps of:

(a) providing a liquid-core waveguide tube having a refractive index less than that of water;

(b) disposing in the tube a water solution of a material which emits chemiluminescence; and (c) detecting the chemiluminescence emitted by the solution;

wherein the liquid-core waveguide tube is made of or coated with an amorphous fluoropolymer which is a copolymer of tetrafluoroethylene and perfluoro-2-2-dimethyl-1,3-dioxole.

18. A photoluminescence detector, comprising:
   (a) a liquid-core waveguide comprising a transparent tube having first and second ends, for containing a liquid which can emit photoluminescence;
   (b) a light source which can provide radiation suitable for exciting the liquid to emit photoluminescence;
   (c) a photodetector, for detecting photoluminescence emitted by the liquid in the liquid-core waveguide tube;
   (d) an optical fiber optically connecting the photodetector to the first end of the liquid-core waveguide tube; and
   (e) a hollow T-shaped member, for holding the optical fiber and the first end of the liquid-core waveguide tube in alignment with one another, and for providing an inlet for the liquid to be contained by the liquid-core waveguide tube.

19. A photoluminescence detector, comprising:
   (a) a liquid-core waveguide comprising a transparent tube having first and second ends, for containing a liquid which can emit photoluminescence;
   (b) a light source which can provide radiation suitable for exciting the liquid to emit photoluminescence;
   (c) a photodetector, for detecting photoluminescence emitted by the liquid in the liquid-core waveguide tube;
   (d) a first passageway for admitting the liquid to the first end of the liquid-core waveguide tube; and
   (e) a second passageway for discharging the liquid from the second end of the liquid-core waveguide tube;

the first and second passageways and the liquid-core waveguide tube being constructed and arranged so that the liquid enters the first passageway, flows through the first passageway into the first end of the liquid-core waveguide tube, flows through the liquid-core waveguide tube, and is discharged from the second end of the liquid-core waveguide tube through the second passageway; the first passageway comprising a first arm of a hollow T-shaped member having first and second arms perpendicular to one another.

20. A photoluminescence detector, comprising:
   (a) a liquid-core waveguide comprising a transparent tube having first and second ends, for containing a liquid which can emit photoluminescence;
   (b) a light source which can provide radiation suitable for exciting the liquid to emit photoluminescence;
   (c) a photodetector, for detecting photoluminescence emitted by the liquid in the liquid-core waveguide tube; and
   (d) an opaque tubular shell enclosing the waveguide and the light source, to provide isolation from external illumination.

21. A photoluminescence detector, comprising:
   (a) a liquid-core waveguide comprising a transparent tube having first and second ends, for containing a liquid which can emit photoluminescence;
   (b) a light source which can provide radiation suitable for exciting the liquid to emit photoluminescence, the radiation from the light source being provided transversely with respect to the liquid-core waveguide tube; and
   (c) a photodetector, for detecting photoluminescence emitted by the liquid in the liquid-core waveguide tube;

wherein the light source circumscribes the liquid-core waveguide tube.

22. A photoluminescence detector, comprising:
   (a) a liquid-core waveguide comprising a transparent tube having first and second ends, for containing a liquid which can emit photoluminescence;
   (b) a light source which can provide radiation suitable for exciting the liquid to emit photoluminescence; and
   (c) a photodetector, for detecting photoluminescence emitted by the liquid in the liquid-core waveguide tube;

wherein the light source circumscribes the liquid-core waveguide tube.

* * * * *